United States Patent [19]

Wright

[11] 4,012,376

[45] Mar. 15, 1977

[54] PHOTOSENSITIVE COLORANT MATERIALS

[75] Inventor: Hal E. Wright, Rochester, N.Y.

[73] Assignee: Eastman Kodak Company, Rochester, N.Y.

[22] Filed: Dec. 29, 1975

[21] Appl. No.: 645,067

[52] U.S. Cl. .......................... 260/240 TC; 96/1.5; 260/240 R; 260/240 CA; 260/240 D; 260/240.9; 260/283 R; 260/283 CN

[51] Int. Cl.² ........................................ C07D 401/10

[58] Field of Search .... 260/240 R, 240 CA, 240 D, 260/240 TC, 240.9, 283 R, 283 CN; 96/1.5 R

[56] References Cited

UNITED STATES PATENTS

| 3,681,068 | 8/1972 | Johnson | 96/1.5 |
|---|---|---|---|
| 3,873,940 | 3/1975 | Drexhage | 260/240 TC |

*Primary Examiner*—Arthur P. Demers
*Attorney, Agent, or Firm*—J. R. Everett

[57] ABSTRACT

Colorant materials which exhibits useful levels of electrical photosensitivity are disclosed. These materials have the formula:

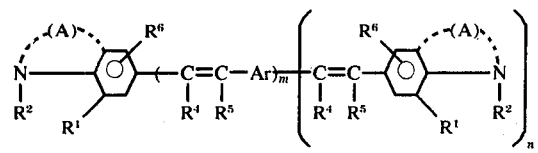

wherein
  $n$ represents 0 or 1,
  $m$ represents 1 or 2,
  Ar represents an aromatic group,
  A represents an alkylene group,
  $R^1$ and $R^2$, when taken together, represent an alkylene group,
  $R^1$, $R^4$, $R^5$, and $R^6$, when taken alone, each represent hydrogen, nitro, cyano, halogen, or one of various specified organo groups, and
  $R^2$, when taken alone, represents hydrogen, an aromatic or an alkyl group.

4 Claims, 1 Drawing Figure

PHOTOSENSITIVE COLORANT MATERIALS

CROSS-REFERENCE TO RELATED APPLICATIONS

Cross-reference is made to Wright and Kaukeinen, U.S. Ser. No. 645,139, filed concurrently herewith and entitled "Electrophoretic Migration Imaging Process, Case B".

FIELD OF THE INVENTION

This invention relates to colorant materials, particularly electrically photosensitive colorant materials, especially useful in electrophoretic migration imaging processes.

BACKGROUND OF THE INVENTION

In the past there has been extensive description in the patent and other technical literature relating to electrophoretic migration imaging processes and colorants useful therein. For example, a description of such processes and colorants may be found in Sugarman, U.S. Pat. No. 2,758,939, issued Aug. 14, 1956; Kaprelian, U.S. Pat. Nos. 2,940,847; 3,100,426; 3,140,175; and 3,143,508; Tulagin et al., U.S. Pat. Nos. 3,384,565; 3,384,488; 3,615,558; Clark, U.S. Pat. No. 3,384,566; and Yeh, U.S. Pat. No. 3,383,993. In addition to the foregoing patent literature directed to conventional photoelectrophoretic migration imaging processes another type of electrophoretic migration imaging process which advantageously provides for image reversal is described in Groner, U.S. patent application Ser. No. 607,650, filed Aug. 25, 1975.

However, regardless of the particular electrophoretic migration imaging process employed, an essential component of any such process is the electrically photosensitive particles. And, of course, to obtain an easy-to-read, visible image it is important that these electrically photosensitive particles be colored as well as electrically photosensitive. Accordingly, as is apparent from the technical literature regarding electrophoretic migration imaging processes, work has been carried on in the past and is continuing to find colorants which possess useful levels of electrical photosensitivity and which exhibit good colorant properites. Thus, for example, various types of electrically photosensitive materials are disclosed for use in electrophoretic migration imaging processes, for example, in Sugarman, U.S. Pat. No. 2,758,939; Kaprelian U.S. Pat. No. 2,940,847; Tulagin et al., U.S. Pat. No. 3,384,488 and U.S. Pat. No. 3,615,558 noted hereinabove.

In large part, the art, to date, has generally selected useful electrically photosensitive or photoconductive pigment materials for electrophoretic migration imaging from known classes of photoconductive materials which may be employed in conventional photoconductive elements, e.g., photoconductive plates, drums, or webs used in electrophotographic office copier devices. For example, both Sugarman and Kaprelian in the above-referenced patents state that electrically photosensitive materials useful in electrophoretic migration imaging processes may be selected from known classes of photoconductive materials. And, the phthalocyanine pigments described as a useful electrically photosensitive material for electrophoretic imaging processes in Tulagin et al., U.S. Pat. No. 3,615,558 have long been known to exhibit useful photoconductive properties.

It is recognized, as set forth above, that many useful electrically photosensitive materials which are employed in electrophoretic migration imaging processes can be and have been selected from known photoconductive materials. However, in accord with the present invention, a class of electrically photosensitive materials has been discovered which is believed to represent a new class of materials. In this regard, it is noted that Johnson, U.S. Pat. No. 3,681,008 issued Aug. 1, 1972, describes certain julolyl group-containing organic photoconductors. However, although the julolyl group is common to the compounds of U.S. Pat. No. 3,681,068 and certain of the electrically photosensitive materials of the present invention, the overall molecular structure of the compounds of U.S. Pat. No. 3,681,068 and those of the present invention is quite different.

Another class of photoconductive materials somewhat similar to those described in the present application are the known organic photoconductive materials including, but not limited to, those materials described in U.S. Pat. Nos. 3,246,983 issued Apr. 19, 1966, 3,567,450 issued Mar. 2, 1971, 3,653,887 issued Apr. 4, 1972, and 3,873,312 issued Mar. 25, 1975. Certain materials within the aforementioned class of organic photoconductive materials have recently been found to possess electrical photosensitivity properties useful in electrophoretic migration imaging processes. These latter materials are described in our copending U.S. patent application Ser. No. 645,005, filed concurrently herewith and entitled *Electrophoretic Migration Imaging Process, Case A*. However, the molecular structure of the electrically photosenstive material used in the present invention is specifically different from that of the organic photoconductors described in the aforementioned patents and also is different from that of the electrically photosensitive material described in our copending patent application. Moreover, the electrically photosensitive material used in the present invention advantageously exhibits improved levels of electrical photosensitivity in comparison to the material described in our copending patent application.

SUMMARY OF THE INVENTION

In accord with the present invention, there has been discovered a new colorant material having the following formula:

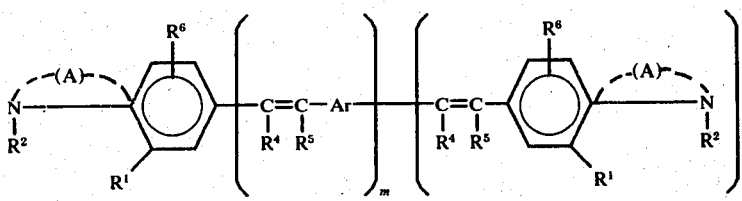

wherein n represents 0 or 1;

m represents the integer 1 or 2;

Ar represents a substituted or unsubstituted, carbocyclic or heterocyclic aromatic ring group, free from any saturated N-heterocyclic ring group fused thereto, and preferably having 6 to about 20 ring group fused thereto, and preferably having 6 to about 20 ring atoms in the aromatic ring, e.g., phenyl, naphthyl, anthryl, etc.;

A represents a substituted or unsubstituted alkylene group having 2 to 5 carbon atoms in the alkylene chain;

each of $R^1$ and $R^2$, when taken together, represent a substituted or unsubstituted alkylene group containing 2 to about 5 carbon atoms in the alkylene chain;

each of $R^1$, $R^4$, $R^5$, and $R^6$, when taken alone, represent hydrogen, nitro, cyano, a halogen such as fluorine, chlorine, bromine or iodine, an alkoxy having 1 to about 8 carbon atoms, a substituted or unsubstituted alkyl having 1 to about 8 carbon atoms in the alkyl group, a substituted or unsubstituted phenyl group, a carboxy ester having 1 to about 4 carbon atoms, an amide having the formula:

$$-CONR_2^7$$

wherein $R^7$ represents hydrogen or a substituted or unsubstituted alkyl or a substituted or unsubstituted as phenyl defined immediately hereinabove; and $R^2$, when taken alone, represents hydrogen, a substituted or unsubstituted alkyl having 1 to about 8 carbon atoms in the alkyl group thereof, substituted or unsubstituted, carbocyclic or heterocyclic aromatic ring group having 6 to about 20 carbon ring atoms.

A variety of different substituents may be present in the above-defined formula in the cases where Ar and A represent substituted aromatic and substituted alkylene groups, respectively. In general, the substituents on Ar and A may be selected from the same class of substituent groups defined above for each of $R^1$, $R^4$, $R^5$, and $R^6$, when taken alone.

When used in an electrophoretic migration imaging process, the colorant materials of the invention are incorporated in charge-bearing, electrically photosensitive particles which are positioned between two spaced electrodes, preferably these particles are contained in an electrically insulating carrier such as an electrically insulating liquid or an electrically insulating, liquefiable matrix material, e.g., a thixotropic or a heat-and/or solvent-softenable material, which is positioned between the spaced electrodes. While so positioned between the spaced electrodes, the photosensitive particles are subjected to an electric field and exposed to a pattern of activating radiation. As a consequence, the charge-bearing, electrically photosensitive particles undergo a radiation-induced variation in their charge polarity and migrate to one or the other of the electrode surfaces to form on at least one of these electrodes an image pattern representing a positive-sense or negative-sense image of the original radiation exposure pattern.

DESCRIPTION OF THE PREFERRED EMBODIMENTS

Figure 1:
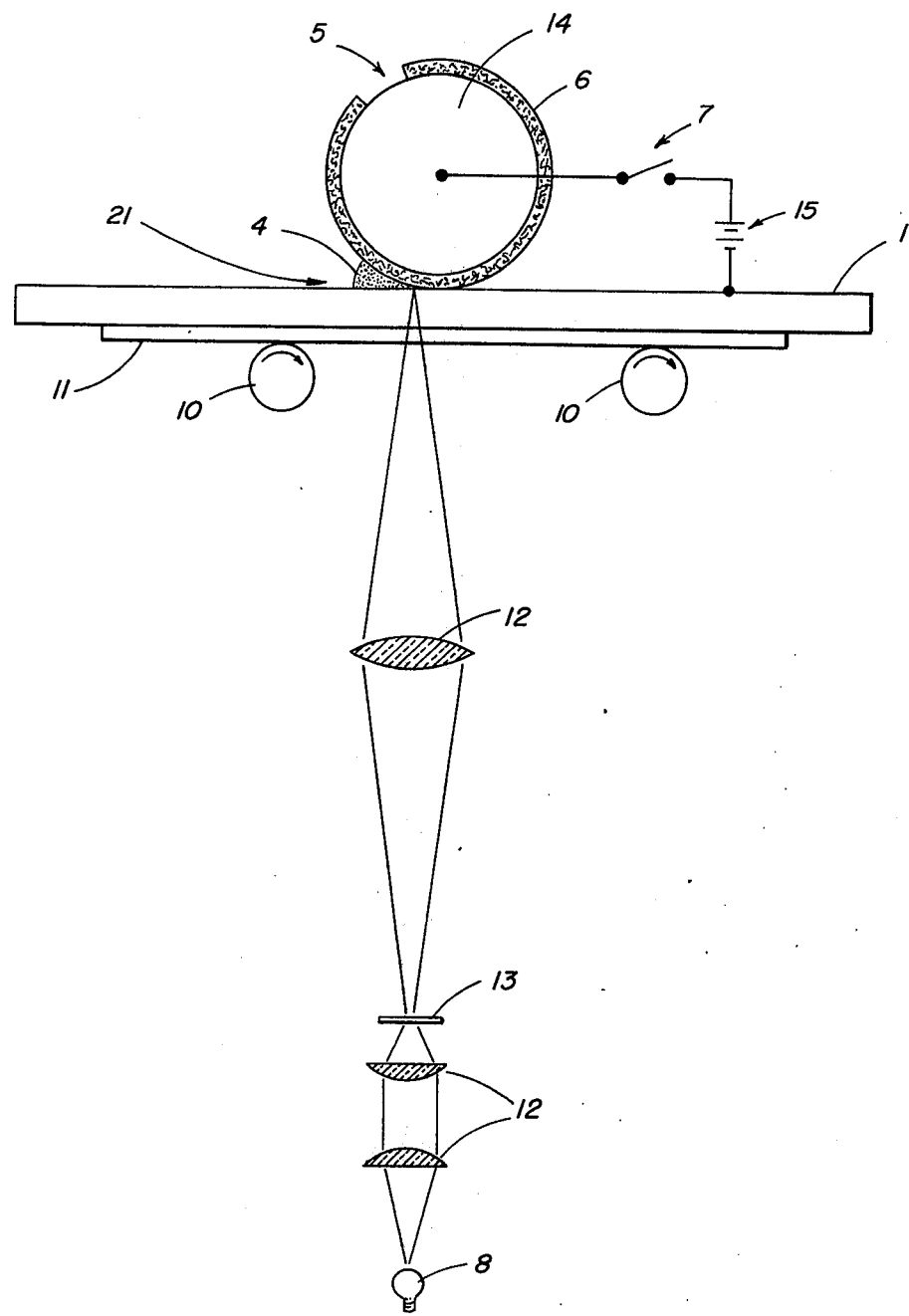
FIG. 1 represents diagrammatically a typical imaging apparatus for carrying out an electrophoretic migration imaging process using the colorant materials of the invention.

In addition to the highly useful levels of electrical photosensitivity exhibited by the materials of formula I above in electrophoretic migration imaging processes, the materials of formula I generally exhibit certain other properties which make these materials quite useful in electrophoretic migration imaging processes. Among other such useful properties, the materials of formula I are typically highly colored materials, generally exhibiting an absorption maxima to visible light having a wavelength greater than 410 nm, preferably in the 420 to 600 nm region of the visible spectrum. Thus, these materials, in general, tend to have a yellow, orange, or magenta hue. Also, the materials of formula I tend to be highly insoluble or only slightly soluble in such conventional organic solvents as aliphatic hydrocarbon solvents such as Isopar G or alkylated aromatic solvents such as Solvesso 100. This latter property of substantial insolubility in conventional organic solvents is advantageous in electrophoretic migration imaging processes, particularly in those embodiments of such processes wherein the electrically photosensitive material is dispersed in particulate form in an electrically insulating carrier such as a conventional aliphatic hydrocarbon liquid to form an electrophoretic migration imaging suspension.

The colorant materials of the present invention typically have formula I illustrated hereinbefore.

The terms "substituted alkylene group" and "substituted alkyl group" and the terms "substituted aromatic ring group" and "substituted phenyl group" as used in the present application are defined to mean those substituents which do not interfere with the electrical photosensitivity properties of the colorants of the invention and which are conventionally recognized in the art as typical substitutents for alkyl and aromatic groups, respectively. A partial listing of representative such substituted alkyl and substituted alkylene groups includes the following materials. Typically, these materials contain 1 to about 8 carbon atoms in the alkyl group thereof. (In the following list, the term "alkyl" is used to include both alkyl and alkylene.)

a. alkoxyalkyl having a total of 2 to about 8 carbon atoms, e.g., ethoxypropyl, methoxybutyl, propoxymethyl, etc., b. aryloxyalkyl, e.g., phenoxyethyl, naphthoxymethyl, phenoxypentyl, etc., c. aminoalkyl, e.g., aminobutyl, aminoethyl, aminopropyl, etc., d. hydroxyalkyl, e.g., hydroxypropyl, hydroxyoctyl, hydroxymethyl, etc., e. aralkyl, e.g., benzyl, phenethyl, ω, ω-diphenylalkyl, etc., f. alkylaminoalkyl, e.g., methylaminopropyl, methylaminoethyl, etc., and also including dialkylaminoalkyl, e.g., diethylaminoethyl, dimethylaminopropyl, propylaminooctyl, etc., g. arylaminoalkyl, e.g., phenylaminoalkyl, diphenylaminoalkyl, N-phenyl-N-ethylaminopentyl, N-phenyl-N-ethylaminohexyl, naphthylaminomethyl, etc., h. nitroalkyl, e.g., nitrobutyl, nitroethyl, nitropentyl, etc., i. cyanoalkyl, e.g., cyanopropyl, cyanobutyl, cyanoethyl, etc.,
j. haloalkyl, e.g., chloromethyl, bromopentyl, chlorooctyl, etc., and
k. alkyl substituted with an acyl group having the formula:

wherein R is hydroxy, hydrogen, aryl, e.g., phenyl, naphthyl, etc., lower alkyl having 1 to about 4 carbon atoms, e.g., methyl, ethyl, propyl, etc., amino including substituted amino, e.g., diloweralkylamino, lower alkoxy having 1 to about 8 carbon atoms, e.g., butoxy, methoxy, etc., aryloxy, e.g., phenoxy, naphthoxy, etc.

A partial listing of representative substituted aromatic and substituted phenyl groups includes the following materials. Typically, the substituent groups on these aromatic materials contain from 1 to about 8 carbon atoms. (In the following list, the term "aryl" is used to include phenyl, as well as other similar carbocyclic aryls such as naphthyl and anthryl.)

a. alkoxyaryl, e.g., ethoxyphenyl, methoxyphenyl, propoxynaphathyl, etc.,
b. aryloxyaryl, e.g., phenoxyphenyl, naphthoxyphenyl, phenoxynaphthyl, etc.,
c. aminoaryl, e.g., aminophenyl, aminonaphthyl, aminoanthryl, etc.,
d. hydroxyaryl, e.g., hydroxyphenyl, hydroxynaphthyl, hydroxyanthryl, etc.,
e. biphenylyl,
f. alkylaminoaryl, e.g., methylaminophenyl, methylaminonaphthyl, etc. and also including dialkylaminoaryl, e.g., diethylaminophenyl, dipropylaminophenyl, etc.,
g. arylaminoaryl, e.g., phenylaminophenyl, diphenylaminophenyl, N-phenyl-N-ethylaminophenyl, naphthylaminophenyl, etc.,
h. nitroaryl, e.g., nitrophenyl, nitronaphthyl, nitroanthryl, etc.,
i. cyanoaryl, e.g., cyanophenyl, cyanonaphthyl, cyanoanthryl, etc.,
j. haloaryl, e.g., chlorophenyl, bromophenyl, chloroanphthyl, etc.,
k. alkaryl, e.g. tolyl, ethylphenyl, propylnaphthyl, etc., and
l. aryl substituted with an acyl group having the formula:

wherein R is hydroxy, hydrogen, lower alkyl having 1 to about 4 carbon atoms, e.g., methyl, ethyl, propyl, butyl, etc., aryl, e.g., phenyl, naphthyl, etc., amino including substituted amino, e.g., diloweralkylamino, lower alkoxy having 1 to about 8 carbon atoms, e.g., butoxy, methoxy, etc., aryloxy, e.g. phenoxy naphthoxy, etc.

Within the class of materials having formula I above, two individual subclasses of materials have been found to exhibit particularly useful properties for electrophoretic migration imaging processes. These two subclasses of materials may be represented by the following structural formulas:

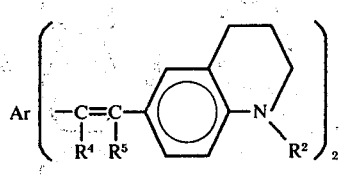

II.

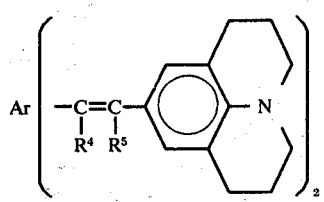

III.

wherein Ar is as defined hereinabove; each of $R^4$ and $R^5$, which may be the same or different, represents hydrogen or a cyano group; and $R^2$ represents a substituted or unsubstituted alkyl group having 1 to 8 carbon atoms in the alkyl group or a substituted or unsubstituted phenyl group, typical substitutents for said substituted alkyl and substituted phenyl groups being selected from those set forth hereinabove.

In general, the photosensitive materials of formula I above which have, to date, been found most useful because of their high degree of photosensitivity and other desirable properties, for example, color separation in multicolor electrophoretic migration imaging processes and the like, tend to exhibit a yellow, orange, or magenta coloration and a maximum absorption wavelength, λmax, within the range of from about 420 to about 600 nm. Although photosensitive materials represented by formulas II and III above have generally been found most useful among the various materials described within the general class having formula I, a variety of different materials within the class defined by formula I have been tested and found to exhibit useful levels of electrical photosensitivity in electrophoretic migration imaging processes. A partial listing of representative such materials is included herein in Table 1

Table 1

| Compound Number | Compound Structure |
| --- | --- |
| 1 | 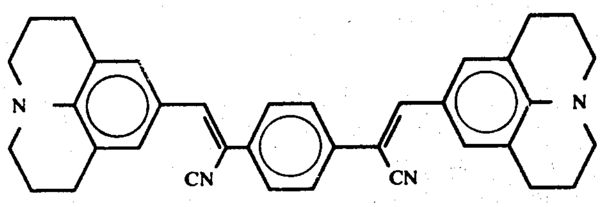 |
| 2 | 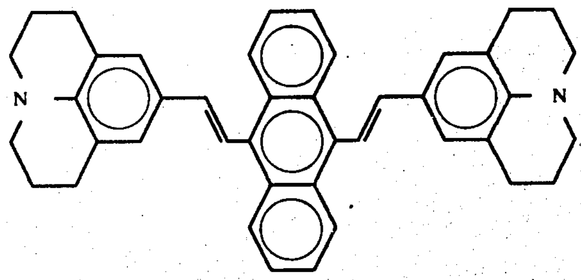 |
| 3 | 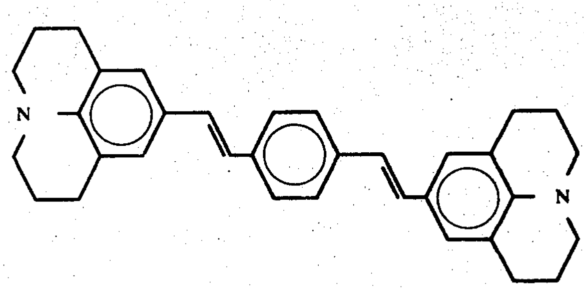 |
| 4 | 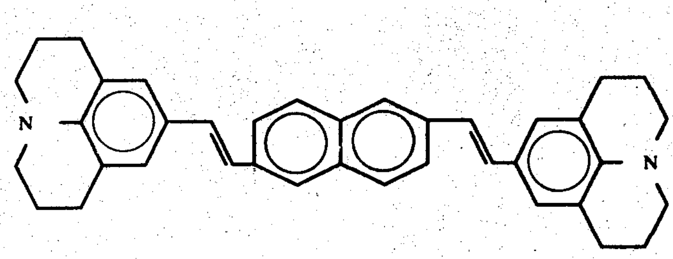 |
| 5 | 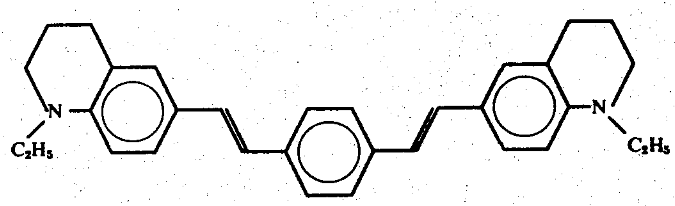 |
| 6 | 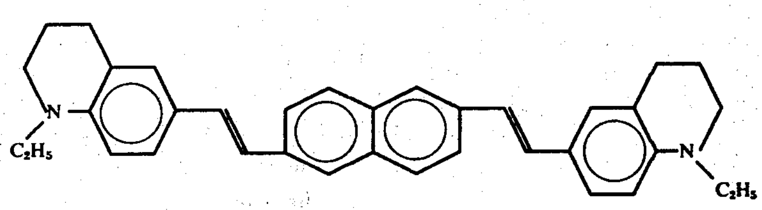 |

Table 1-continued
| Compound Number | Compound Structure |
|---|---|
| 7 | 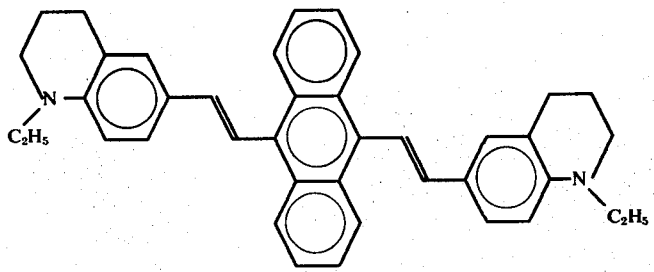 |
| 8 | 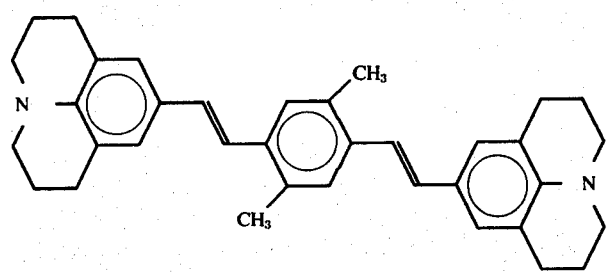 |
| 9 | 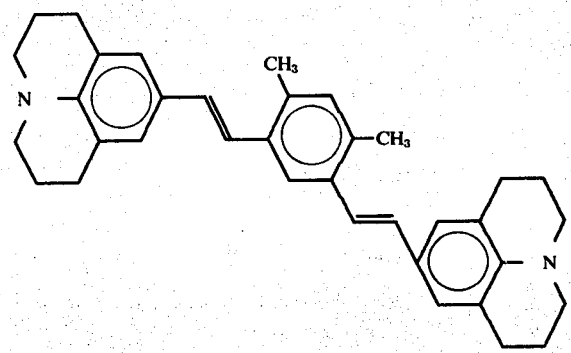 |
| 10 | 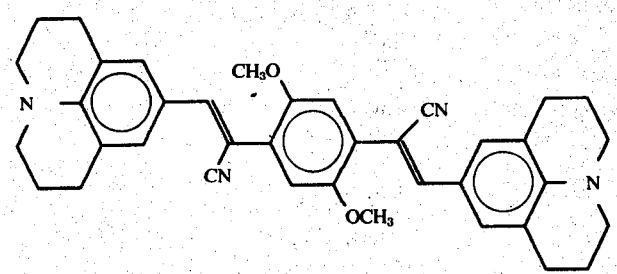 |
| 11 | 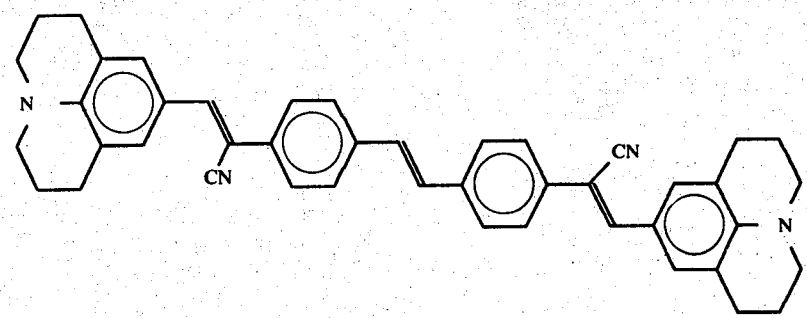 |

Table 1-continued

| Compound Number | Compound Structure |
|---|---|
| 12 | 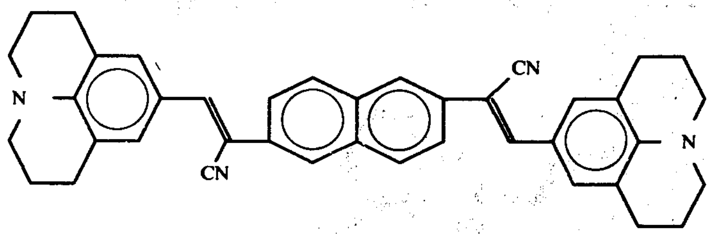 |
| 13 | 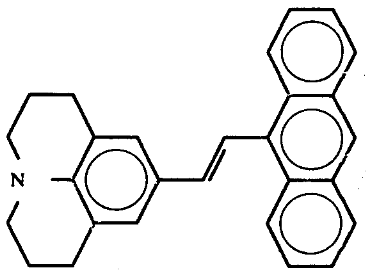 |
| 14 | 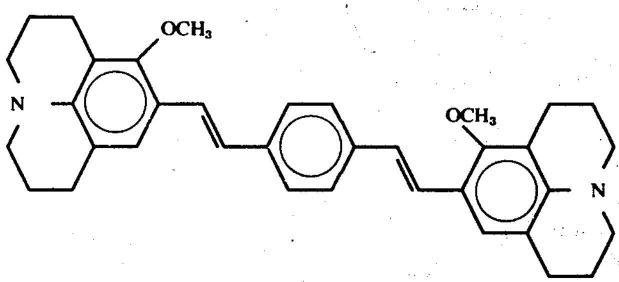 |

As indicated hereinabove, the electrically photosensitive colorant material described herein can be used in the preparation of electrically photosensitive imaging particles of electrophoretic migration imaging processes. In general, electrically photosensitive particles useful in such processes have an average particle size within the range of from about 0.01 micron to about 20 microns, preferably from about 0.01 to about 5 microns. Typically, these particles are composed of one or more colorant materials such as those described in the present invention. However, these electrically photosensitive particles may also contain various non-photosensitive materials such as electrically insulating polymers, charge control agents, various organic and inorganic fillers, as well as various additional dyes or pigment materials to change or enhance various colorant and physical properties of the electrically photosensitive particle. In addition, such electrically photosensitive particles may contain other photosensitive materials such as various sensitizing dyes and/or chemical sensitizers to alter or enhance their response characteristics to activating radiation.

When used in an electrophoretic migration imaging process, the electrically photosensitive material described herein as shown in formula I hereinabove is typically positioned, in particulate form, between two or more spaced electrodes, one or both of which typically being transparent to radiation to which the electrically photosensitive material is light sensitive, i.e., activating radiation. Although the electrically photosensitive material, in particulate form, may be dispersed simply as a dry powder between two spaced electrodes and then subjected to a typical electrophoretic migration imaging operation such as that described in Sugarman, U.S. Pat. No. 2,758,939 referenced hereinabove, it is more typical to disperse the electrically photosensitive particulate material in an electrically insulating carrier, such as an electrically insulating liquid, or an electrically insulating, liquefiable matrix material, such as a heat and/or solvent softenable polymeric material, or a thixotropic polymeric material. Typically, when one employs such a dispersion of electrically photosensitive particulate material and electrically insulating carrier material between the spaced electrodes of an electrophoretic migration imaging system, it is conventional to employ from about 0.05 parts to about 2.0 parts of electrically photosensitive particulate material for each 10 parts by weight of electrically insulating carrier material.

As indicated above, when the electrically photosensitive particles used in the present invention are dispersed in an electrically insulating carrier material, such carrier material may assume a variety of physical forms and may be selected from a variety of different materials. For example, the carrier material may be a matrix of an electrically insulating, normally solid polymeric material capable of being softened or liquefied upon application of heat, solvent, and/or pressure so that the electrically photosensitive particulate material dispersed therein can migrate through the matrix. In another, more typical embodiment of the invention, the carrier material can comprise an electrically insulating liquid such as decane, paraffin, Sohio Oderless Solvent 3440 (a kerosene fraction marketed by the Standard Oil Company, Ohio), various isoparaffinic hydrocarbon liquids such as those sold under the trademark Isopar G by Exxon Corporation and having a boiling point in the range of 145° C. to 186° C., various halogenated hydrocarbons such as carbon tetrachloride, trichloromonofluoromethane, and the like, various alkylated aromatic hydrocarbon liquids such as the alkylated benzenes, for example, xylenes, and other alkylated aromatic hydrocarbons such as are described in U.S. Pat. No. 2,899,335. An example of one such useful alkylated aromatic hydrocarbon liquid which is commercially available is Solvesso 100 made by Exxon Corp. Solvesso 100 has a boiling point in the range of about 157° C. to about 177° C. and is composed of 9 percent xylene, 16 percent of other monoalkyl benzenes, 34 percent dialkyl benzenes, 37 percent trialkyl benzenes, and 4 percent aliphatics. Typically, whether solid or liquid at normal room temperatures, i.e., 22° C., the electrically insulating carrier material used in the present invention is a material having a resistivity greater than about $10^9$ ohm-cms, preferably greater than about $10^{12}$ ohm-cm. When the electrically photosensitive particles used in the present invention are incorporated in a carrier material, such as one of the above-described electrically insulating liquids, various other addenda may also be incorporated in the resultant imaging suspension. For example, various charge control agents may be incorporated in such a suspension to improve the uniformity of charge polarity of the electrically photosensitive particles dispersed in the liquid suspension. Such charge control agents are well known in the field of liquid electrographic developer compositions where they are employed for purposes substantially similar to that described herein. Thus, extensive discussion of these materials herein is deemed unnecessary. These materials are typically polymeric materials incorporated by admixture thereto into the liquid carrier vehicle of the suspension. In addition to, and possibly related to, the aforementioned enhancement of uniform charge polarity, it has been found that the charge control agents often provide more stable suspensions, i.e., suspensions which exhibit substantially less settling out of the dispersed photosensitive particles.

In addition to the foregoing charge control agent materials, various polymeric binder materials such as various natural, semi-synthetic or synthetic resins, may be dispersed or dissolved in the electrically insulating carrier to serve as a fixing material for the final photosensitive particle image formed on one of the spaced electrodes used in electrophoretic migration imaging systems. Here again, the use of such fixing addenda is conventional and well known in the closely related art of liquid electrographic developer compositions so that extended discussion thereof is unnecessary herein.

The utility of the colorants of the present invention will be described in more detail with reference to the accompanying drawing, FIG. 1, which illustrates an apparatus which carries out a electrophoretic migration imaging process.

FIG. 1 shows a transparent electrode 1 supported by two rubber drive rollers 10 capable of imparting a translating motion to electrode 1 in the direction of the arrow. Electrode 1 may be composed of a layer of optically transparent material, such as glass or an electrically insulating, transparent polymeric support such as polyethylene terephthalate, covered with a thin, optically transparent, conductive layer such as tin oxide, nickel, and the like. Optionally, depending upon the particular type of electrophoretic migration imaging process desired, the surface of electrode 1 may bear a "dark charge exchange" material, such as a solid solution of an electrically insulating polymer and 2,4,7,trinitro-9-fluorenone as described in Groner, U.S. patent application Ser. No. 607,650, filed Aug. 25, 1975.

Spaced opposite electrode 1 and in pressure contact therewith is a second electrode 5, an idler roller which serves as a counter electrode to electrode 1 for producing the electric field used in the electrophoretic migration imaging process. Typically, electrode 5 has on the surface thereof a thin, electrically insulating layer 6. Electrode 5 is connected to one side of the power source 15 by switch 7. The opposite side of the power source 15 is connected to electrode 1 so that as an exposure takes place, switch 7 is closed and an electric field is applied to the electrically photosensitive particulate material 4 which is positioned between electrodes 1 and 5. Typically electrically photosensitive particulate material 4 is dispersed in an electrically insulating carrier material such as described hereinabove.

The electrically photosensitive particulate material 4 may be positioned between electrodes 1 and 5 by applying material 4 to either or both of the surfaces of electrodes 1 and 5 prior to the imaging process or by injecting electrically photosensitive imaging material 4 between electrodes 1 and 5 during the electrophoretic migration imaging process.

As shown in FIG. 1, exposure of electrically photosensitive particulate material 4 takes place by use of an exposure system consisting of light source 8, an original image 11 to be reproduced, such as a photographic transparency, a lens system 12, and any necessary or desirable radiation filters 13, such as color filters, whereby electrically photosensitive material 4 is irradiated with a pattern of activiating radiation corresponding to original image 11. Although the electrophoretic migration imaging system represented in FIG. 1 shows electrode 1 to be transparent to activating radiation from light source 8, it is possible to irradiate electrically photosensitive particulate material 4 in the nip 21 between electrodes 1 and 5 without either of electrodes 1 or 5 being transparent. In such a system, although not shown in FIG. 1, the exposure source 8 and lens system 12 is arranged so that image material 4 is exposed in the nip or gap 21 between electrodes 1 and 5.

As shown in FIG. 1, electrode 5 is a roller electrode having a conductive core 14 connected to power source 15. The core is in turn covered with a layer of insulating material 6, for example, baryta paper. Insulating material 6 serves to prevent or at least substantially reduce the capability of electrically photosensitive particulate material 4 to undergo a radiation induced charge alteration upon interaction with electrode 5. Hence, the term "blocking electrode" may be used, as is conventional in the art of electrophoretic migration imaging, to refer to electrode 5.

Although electrode 5 is shown as a roller electrode and electrode 1 is shown as essentially a translatable, flat plate electrode in FIG. 1, either or both of these electrodes may assume a variety of different shapes such as a web electrode, rotating drum electrode, plate electrode, and the like as is well known in the field of electrophoretic migration imaging. In general, during a typical electrophoretic migration imaging process wherein electrically photosensitive material 4 is dispersed in an electrically insulating, liquid carrier, electrodes 1 and 5 are spaced such that they are in pressure contact or very close to one another during the electrophoretic migration imaging process, e.g., less than 50 microns apart. However, where electrically photosensitive particulate material 4 is dispersed simply in an air gap between electrodes 1 and 5 or in a carrier such as a layer of heat-softenable or other liquefiable material coated as a separate layer on electrode 1 and/or 5, these electrodes may be spaced more than 50 microns apart during the imaging process.

The strength of the electric field imposed between electrodes 1 and 5 during an electrophoretic migration imaging process may vary considerably; however, it has generally been found that optimum image density and resolution are obtained by increasing the field strength to as high a level as possible without causing electrical breakdown of the carrier medium in the electrode gap. For example, when electrically insulating liquids such as isoparaffinic hydrocarbons are used as the carrier in the imaging apparatus of FIG. 1, the applied voltage across electrodes 1 and 5 typically is within the range of from about 100 volts to about 4 kilovolts or higher.

As explained hereinabove, image formation occurs in electrophoretic migration imaging processes as the result of the combined action of activating radiation and electric field on the electrically photosensitive particulate material 4 disposed between electrodes 1 and 5 in the attached drawing. Typically, for best results, field application and exposure to activating radiation occur concurrently. However, as would be expected, by appropriate selection of various process parameters such as field strength, activating radiation intensity, incorporation of suitable light sensitive addenda in or together with the electrically photosensitive material of formula I used in the present invention, e.g., by incorporation of a persistent photoconductive material, and the like, it is possible to alter the timing of the exposure and field application events so that one may use sequential exposure and field application events rather than concurrent field application and exposure events.

When disposed between imaging electrodes 1 and 5 of FIG. 1, electrically photosensitive particulate material 4 exhibits an electrostatic charge polarity, either as a result of triboelectric interaction of the particles or as a result of the particles interacting with the carrier material in which they are dispersed, for example, an electrically insulating liquid, such as occurs in conventional liquid electrographic developing compositions composed of toner particles which acquire a charge upon being dispersed in an electrically insulating carrier liquid.

Image discrimination occurs in the electrophoretic migration imaging process of FIG. 1 as a result of the combined application of electric field and activating radiation on the electrically photosensitive particulate material dispersed between electrodes 1 and 5 of the apparatus shown in FIG. 1. That is, in a typical imaging operation, upon application of an electric field between electrodes 1 and 5, the particles 4 of charge-bearing, electrically photosensitive material are attracted in the dark to either electrode 1 or 5, depending upon which of these electrodes has a polarity opposite to that of the original charge polarity acquired by the electriclly photosensitive particles. And, upon exposing particles 4 to activating electromagnetic radiation, it is theorized that there occurs neutralization or reversal of the charge polarity associated with either the exposed or unexposed particles. In typical electrophoretic migration imaging systems wherein electrode 1 bears a conductive surface, the exposed, electrically photosensitive particles 4, upon coming into electrical contact (not necessarily physical contact) with such conductive surface, undergo an alteration (usually a reversal) of their original charge polarity as a result of the combined application of electric field and activating radiation. Alternatively, in the case wherein the surface of electrode 1 bears a dark charge exchange material as described in Groner, U.S. patent application Ser. No. 607,650, filed Aug. 25, 1975, one obtains reversal of the charge polarity of the unexposed particles, while maintaining the original charge polarity of the exposed electrically photosensitive particles, as these particles come into electrical contact with the dark charge exchange surface of electrode 1. In any case, upon the application of electric field and activating radiation to electrically photosensitive particulate material 4 disposed betwen electrodes 1 and 5 of the apparatus shown in FIG. 1, one can effectively obtain image discrimination so that an image pattern is formed by the electrically photosensitive particles which corresponds to the original pattern of activating radiation. Typically, using the apparatus shown in FIG. 1, one obtains a visible image on the surface of electrode 1 and a complementary image pattern on the surface of electrode 5.

Subsequent to the application of the electric field and exposure to activating radiation, the images which are formed on the surface of electrodes 1 and/or 5 of the apparatus shown in FIG. 1 may be temporarily or permanently fixed to these electrodes or may be transferred to a final image receiving element. Fixing of the final particle image can be effected by various techniques, for example, by applying a resinous coating over the surface of the image bearing substrate. For example, if electrically photosensitive particles 4 are dispersed in a liquid carrier between electrodes 1 and 5, one may fix the image or images formed on the surface of electrodes 1 and/or 5 by incorporating a polymeric binder material in the carrier liquid. Many such binders (which are well known for use in liquid electrophotographic liquid developers) are known to acquire a charge polarity upon being admixed in a carrier liquid and therefore will, themselves, electrophoretically migrate to the surface of one or the other of the electrodes. Alternatively, a coating of a resinous binder (which has been admixed in the carrier liquid, may be formed on the surfaces of electrodes 1 and/or 5 upon evaporation of the liquid carrier.

The electrically photosensitive colorant material used in the present invention may be used to form monochrome images, or the material may be admixed with other electrically photosensitive material of proper color and photosensitivity and used form polychrome images. As indicated, many of the electrically photosensitive colorant materials having formula I described herein have an especially useful yellow or orange hue and therefore are particularly suited for use in polychrome imaging processes which employ a mixture of two or more differently colored electrically photosensitive particles, e.g., a mixture of cyan particles which are principally sensitive to red light, magenta particles which are principally sensitive to green light, and yellow or orange particles containing the electrically photosensitive colorant materials described in the present invention which are principally sensitive to blue light. When such a mixture of multicolored electrically photosensitive particles is formed, for example, in an electrically insulating carrier liquid, this liquid mixture of particulate material exhibits a black coloration. Preferably, the specific cyan, magenta, and yellow particles selected for use in such a polychrome imaging process are chosen so that their spectral response curves do not appreciable overlap whereby color separation and subtractive multicolor image reproduction can be achieved.

The following examples illustrate the invention, the parts and percentages being by weight unless otherwise stated.

In the following examples, the compounds of formula I of the present invention were prepared by the reaction of an aldehyde or ketone with a compound bearing an active methylene group. A general reaction sequence for this synthesis is illustrated below:

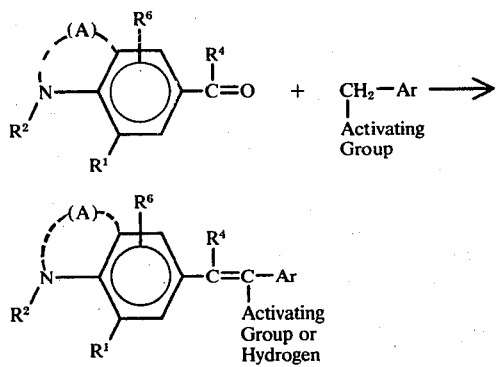

where $R^1$, $R^2$, $R^4$, $R^6$, A and Ar are as defined in formula I. One can change $n$ in formula I from 0 (as would occur using the above-noted reaction precedure) to 1 by using a compound containing two, rather than one, active methylene groups. The general formula for such a compound is as follows:

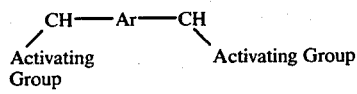

where Ar is as defined in formula I. In addition, one can change $m$ in formula I from 1 (as would occur using the above-noted reaction procedure) to 2 by using a compound having either of the following two formulas:

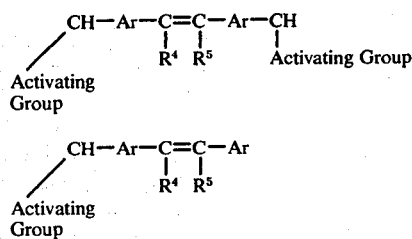

where Ar, $R^4$, and $R^5$ are as defined in formula I. A wide variety of well-known activating groups can be employed in the above-identified reaction procedure as will be apparent to those skilled in the art. See, for example, H. O. House, *Modern Synthetic Reactions*, 2nd edition, W. A. Benjamin, Inc., p. 492–495, (1972). Several detailed preparation schemes are presented hereinafter as illustrative of the general reaction procedure described above.

EXAMPLE 1

Preparation of 6,6'-(p-phenylenedivinylene)bis(N-ethyl-1,2,3,4-tetrahydroquinoline) compound No. 5 of Table 1

To a well-stirred slurry of 2.43 g. of sodium methoxide in 40 ml. of dimethylformamide was added dropwise, under a nitrogen atmosphere, a solution of 7.95 g. of 6-formyl-N-ethyl-1,2,3,4-tetrahydroquinoline and 7.56 g. of tetraethyl-p-xylylenediphosphonate in 40 ml. of dimethylformamide. After stirring for about 36 hours at room temperature, the reaction mixture was poured into 1½ l. water. The solid material was collected and recrystallized two times from xylene. The solid material exhibited a melting point of 213°–215° C (d) and was identified as compound No. 5 of Table 1 using standard spectroscopic techniques and analyses to determine its molecular structure.

EXAMPLE 2

Preparation of 9,9'-(α,α'-dicyano-p-phenylenedivinylene)bis-juloidene, compound 1 of Table 1

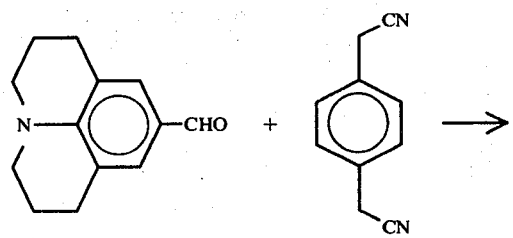

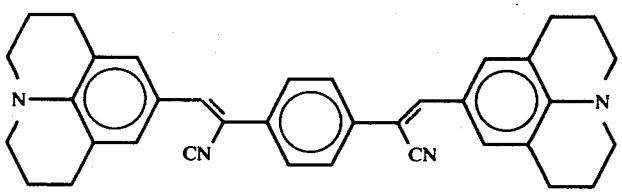

-continued

A mixture of 6.23 g. (0.031 mole) of 9-formyljulolidene 2.34 g. (0.015 mole) of p-benzene diacetonitrile, 6 ml. of piperidine, 3.6 ml of acetic acid, 15 ml of n-propyl alcohol, and 50 ml. of benzene was refluxed under a nitrogen atmosphere with a Dean-Start trap for about 36 hrs. The reaction mixture was allowed to cool and the crystalline material collected. The material was recrystallized twice from xylene and exhibited a m.p. 284°–286° (d) C.; it was identified as compound 1 of Table 1 by use of standard spectroscopic techniques and analyses.

Image Evaluation Apparatus

An image evaluation apparatus was used in each of the succeeding examples to carry out the electrophoretic migration imaging process described herein. This apparatus was a device of the type illustrated in FIG. 1. In this apparatus, a translating NESATRON ( a trademark of PPG for a conductive indium oxide sputtered glass) glass plate served as electrode 1 and was in pressure contact with electrode 5 consisting of a 10 centimeter diameter, resilient polymer coated aluminum roller 14 covered with an insulating layer 6 composed of paper bearing an overcoat of poly(vinyl butyral) and $TiO_2$ particles. NESATRON plate 1 was supported by two 2.8 cm. diameter rubber drive rollers 10 positioned beneath NESATRON plate 1 such that a 2.5 cm. opening, symmetric with the axis of aluminum roller 14, existed to allow exposure of electrically photosensitive particles 4 to activating radiation. The original transparency 11 to be reproduced was taped to the back side of NESATRON plate 1. The exposing activating radiation was supplied from a light source 8 consisting of a Kodak Carousel projector having a maximum exposure intensity of 3500 footcandles at the NESATRON glass plate exposure plane. A Kodak Wratten 2A filter was placed in the beam of exposing radiation so that no exposure was made in the ultraviolet portion of the spectrum. The voltage between the electrode 5 and NESATRON plate 1 was 1 kilovolt. NESATRON plate 1 was negative polarity in the case where electrically photosensitive particulate material 4 carried a positive electrostatic charge, and NESATRON plate 1 was positive in the case where electrically photosensitive electrostatically charged particles were negatively charged. The translational speed of NESATRON plate 1 was variable between about 1.25 cm. and about 30 cm. per second. In the following examples, image formation occurs on the surfaces of NESATRON glass plate 1 and electrode 5 after simultaneous application of light exposure and electric field to electrically photosensitive particulate material 4. In this image evaluation apparatus, each different type of material to be evaluated for use as electrically photosensitive particulate material 4 was admixed with a liquid carrier as described below to form a liquid imaging dispersion which was placed in nip 21 between the electrodes 1 and 5. If the material being evaluated for use as material 4 possessed a useful level of electrical photosensitivity, one obtained a negative-appearing image reproduction of original 11 on electrode 5 and a complementary image on electrode 1.

Imaging Dispersion Preparation

In the following examples a series of 8 different imaging dispersions were prepared to evaluate various types of materials for elctrical photosensitivity. These dispersions were prepared by ball-milling the various materials to be tested for electrical photosensitivity at high concentration with a polymeric charge control agent and then diluting the resultant mixture with another polymer solution. The exact ratios of the various materials used in the initial high concentration ball-mill concentrate and subsequent polymer solution are outlined below:

Ball-Mill Concentrate 1. 1 gram of material to be tested for electrical photosensitive properties,
2. 1 gram of polymeric charge control agent consisting of a copolymer of vinyl toluene, laurly methacrylate, lithium methacrylate, and methacrylic acid, the monomeric weight percent ratio of vinyl toluene to laurly methacrylate to lithium methacrylate to methacrylic acid being as follows: 56:40:3.6:0.4, respectively.
3. 110 grams of stainless steel balls having a diameter of about 3 mm., and
4. 12.2 grams of carrier liquid consisting of Solvesso 100 (purchased from the Exxon Corporation).

Each of the ball-mill concentrates having the above-noted composition were ball-milled in a 125 milliliter glass jar at 115 revolutions per minute for at least one week. The ball-mill concentrates were then diluted by adding 35.8 grams of a 40% by weight solution of Piccotex 100 (a styrenetoluene copolymer purchased from the Pennsylvania Industrial Chemical Corporation) in Isopar G. The resulting diluted imaging dispersion was ball-milled for at least one day.

EXAMPLES 3–10

Table 2 hereinafter contains the results for nine different colorant materials evaluated for electrical photosensitivity properties for use in electrophoretic migration imaging. The first eight materials evaluated in Table 2 correspond to materials 1–7 and 11 set forth hereinbefore in Table 1. Each of these eight different materials had a formula within structural formula I set forth hereinbefore and exhibited electrical photosensitivity when tested in a migration imaging process using the image evaluation apparatus as outlined above. However, the last material, i.e., the control material, had a structural formula outside the scope of formula I and therefore outside the scope of the present invention. A control material was used in Examples 3–10 to demonstrate the highly useful levels of electrical photosensitivity suitable for electrophoretic migration imaging processes exhibited by the materials of the present invention (i.e., materials 1–7 and 11). The material selected as a control was used because it represents a material known to have good electrical photosensitivity suitable for use in electrophoretic migration imaging processes. In Table 2, the speed of the NESATRON plate electrode 1 used in the above-described image evaluation apparatus is noted as well as various other evaluation parameters. Since materials 1–7 and 11 are identical to compounds 1–7 and 11 of Table 1, their structure is not presented in Table 2. In general, the colorants tested in Table 2 provided images having relatively good densities with a maximum reflection density in the range of from about 0.7 to about 1.8 and with acceptable minimum density in clear background image areas. The foregoing densities were measured on the images formed on electrode 5. In general, better densities, especially improved minimum densities for the clear background image areas, were obtained for the colorants of the present invention in comparison to the control colorant of Table 2. In addition, as shown in Table 2, many of the colorants of the present invention exhibited greater light sensitivty than the control.

was used to form multicolor electrophoretic migration images using the above-described image evaluation apparatus. In this multicolor imaging example, the intensity of the imagewise exposure on the plane of the NESATRON plate was 3500 footcandles and the translational speed of the NESATRON plate during the multicolor imaging operation was about 10 cm./sec. A Kodak Wratten 2A filter was included in the exposure beam of light along with an interference cutoff filter (30% transmittance of 665 nm.) so that only the visible portion of the spectrum was used in the exposure. The voltage between electrode 5 and NESATRON plate 1 was maintained at 1 kilovolt during the imaging operation. As a result, it was found that a good quality three-color negative-to-positive print was formed on blocking layer 6 of electrode 5 and, also, a good positive-to-positive multicolor print was formed on the surface of NESATRON plate 1.

EXAMPLE 12

The procedures described above in Example 11 to obtain polychrome electrophoretic migration imaging was repreated, except that the yellow pigment used in the yellow dispersion of this example was material 5 of Table 2

| Compound Number | Intensity of exposing radiation at exposure plane (footcandles) | NESATRON Glass Speed (cm/sec) | λmax (nm) |
| --- | --- | --- | --- |
| 1 | 25 | 25 | 560 |
| 2 | 100 | 25 | 510 |
| 3 | 250 | 25 | 490 |
| 4 | 250 | 25 | 460 |
| 5 | 250 | 25 | 460 |
| 6 | 250 | 25 | — |
| 7 | 25 | 25 | 500 |
| 11 | 25 | 25 | 520 |
| Control having the formula | 250 | 25 | 470 |

$(C_2H_5)_2N-\bigcirc-CH=CH-\bigcirc-CH=CH-\bigcirc-N(C_2H_5)_2$

EXAMPLE 11

In this example, the use of the materials described by structural formula I herein in a polychrome electrophoretic migration imaging process was demonstrated. In this example, three separate cyan, magenta and yellow monochrome dispersions were prepared. Each such monochrome dispersion was prepared using the dispersion preparation technique outlined above. The electrically photosensitive material used as the photosensitive and colorant material in the cyan dispersion was Cyan Blue GTNF, Colour Index No. 74160, a beta form of copper phthalocyanine available from American Cyanamid. The electrically photosensitive material used as the photosensitive and colorant material in the magenta dispersion was Sandorin Brilliant Red 5BL, a quinacridone pigment (apparently similar or identical to Pigment Red 192 of the Colour Index) available from the Sandoz Corporation. The electrically photosensitive material used as the photosensitive and colorant material of the yellow dispersion was material of Tables 1 and 2, i.e., 9,9'-(p-phenylene-divinylene)bis julolidene. After preparing each of the above-described monochrome dispersions, these three dispersions were admixed together in a volume ratio of cyan to magenta to yellow of 1:1:2. The resultant "trimix" dispersion Tables 1 and 2, i.e., 6,6'-(p-phenylene-divinylene)-bis(N-ethyl-1,2,3,4-tetrahydroquinoline). The results of this example were similar to Example 12 in that it was again found that a good quality three-color negative-to-positive print was formed on blocking layer 6 of electrode 5 and, also, a good positive-to-positive multicolor print was formed on the surface of NESATRON plate 1.

EXAMPLES 13–16

Colorant materials 8, 9, 10, and 12 of Table 1 were evaluated for electrical photosensitivity in a manner identical to that described in Examples 3–10. Each of materials 8, 9, 10, and 12 exhibited useful levels of electrical photosensitivity, with materials 8, 10, and 12 showing especially useful levels of photosensitivity equivalent to or better than that exhibited by materials 3–6 of Table 2.

Although the colorant materials of the present invention have been found particularly useful in electrophoretic migration imaging processes as indicated hereinabove, it is apparent that these materials can be employed as useful pigment materials in a variety of other applications. For example, these materials may be used as a light-sensitive component in various light-sensitive compositions, e.g., conventional electrophotographic photoconductive compositions containing one or more photosensitive colorants of the present invention in admixture with a film-forming, electrically insulating polymeric binder and optionally one or more additional light-sensitive and/or sensitizer materials. In addition, the colorants of the invention can be used in many other areas where, for example, colorants or pigments are desired. Such areas would include, for instance, printing inks, pastes, paints, molding powders, electrostatic toner powders, etc.

The invention has been described in detail with particular reference to certain preferred embodiments thereof, but it will be understood that variations and modifications can be effected within the spirit and scope of the invention.

I claim:

1. An electrically photosensitive colorant having the formula:

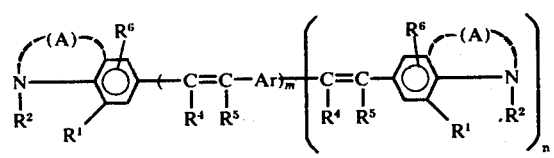

wherein
n represents 0 or 1; m represents the integer 1 or 2;
Ar represents a substituted or unsubstituted aromatic ring group, free from any saturated N-heterocyclic ring group fused thereto, having 6 to 20 ring atoms in the aromatic ring;
A represents a substituted or unsubstituted alkylene group having 2 to 5 carbon atoms in the alkylene chain;
each of $R^1$ and $R^2$, when taken together, represents a substituted or unsubstituted alkylene group having 2 to 5 carbon atoms in the alkylene chain;
each of $R^1$, $R^4$, $R^5$, and $R^6$, when taken alone, represents hydrogen, nitro, cyano, halogen, alkoxy having 1 to 8 carbon atoms, substituted or unsubstituted alkyl having 1 to 8 carbon atoms in the alkyl group, substituted or unsubstituted phenyl, carboxy ester having 1 to 4 carbon atoms, or an amide having the formula:

$$-CONR_2^7$$

wherein
$R^7$ represents hydrogen or substituted or unsubstituted phenyl or substituted or unsubstituted alkyl having 1 to 8 carbon atoms in the alkyl group; and
$R^2$, when taken alone, represents hydrogen, substituted or unsubstituted alkyl having 1 to 8 carbon atoms in the alkyl group, or substituted or unsubstituted aromatic ring group having 6 to 20 carbon ring atoms.

2. An electrically photosensitive colorant component having the following formula:

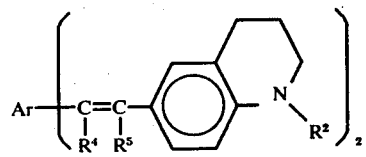

wherein
Ar represents a substituted or unsubstituted, aromatic ring group having 6 to 20 ring atoms in the aromatic ring;
each of $R^4$ and $R^5$, which may be the same or different, represents hydrogen or cyano; and
$R^2$ represents a substituted or unsubstituted alkyl group having 1 to 8 carbon atoms in the alkyl group or a substituted or unsubstituted phenyl group.

3. An electrically photosensitive colorant component having the following formula:

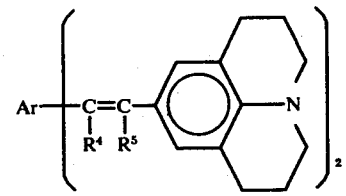

wherein
Ar represents a substituted or unsubstituted, aromatic ring group having 6 to 20 ring atoms in the aromatic ring; and
each of $R^4$ and $R^5$, which may be the same or different, represents hydrogen or cyano.

4. An electrically photosensitive colorant having one of the following formulas:

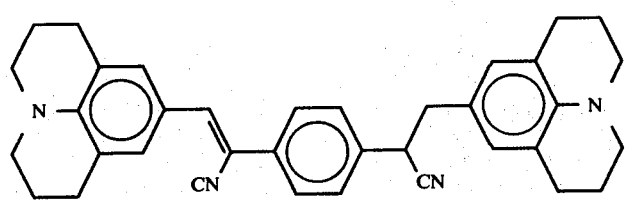

-continued
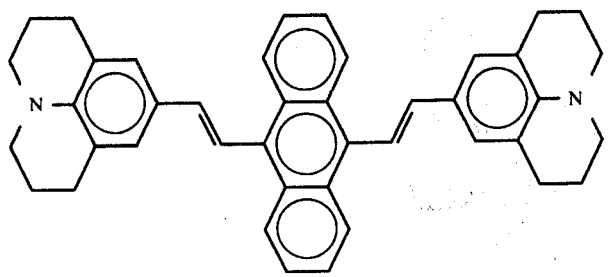
b.
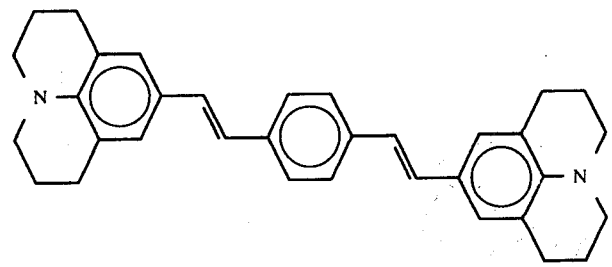
c.
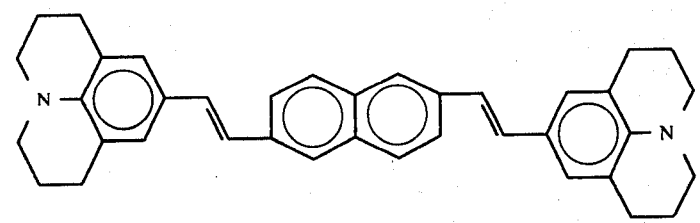
d.
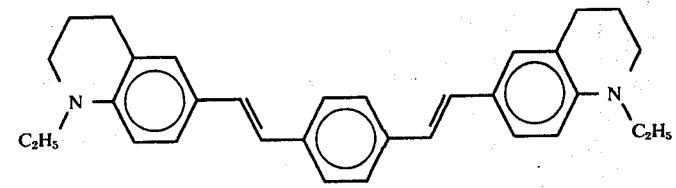
e.
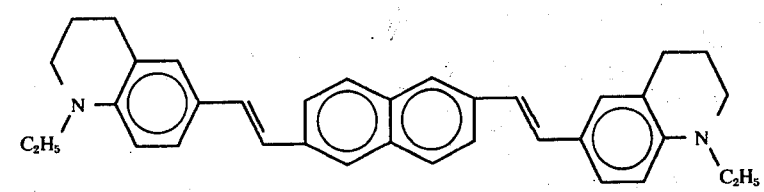
f.
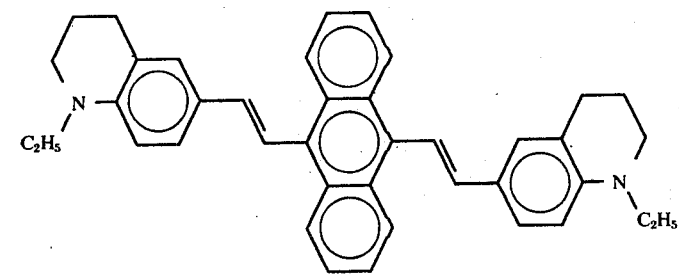
g.

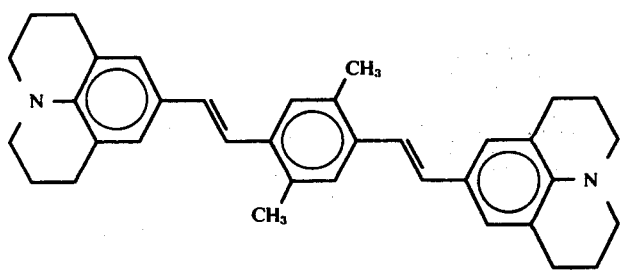
h.
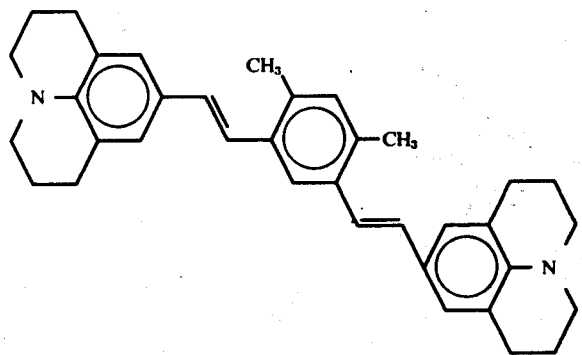
i.
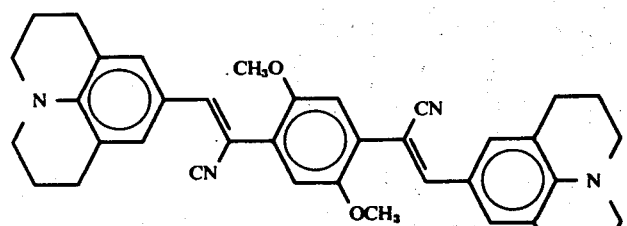
j.
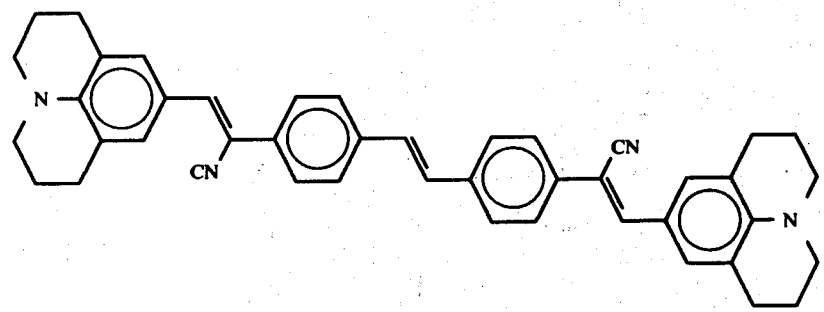
k.
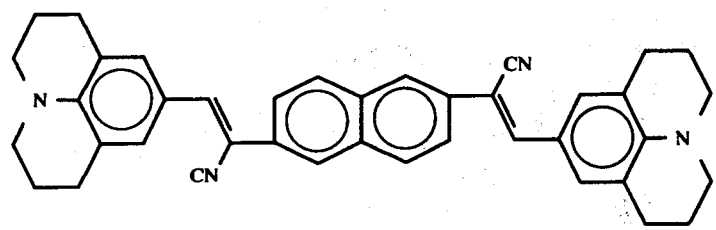
l.

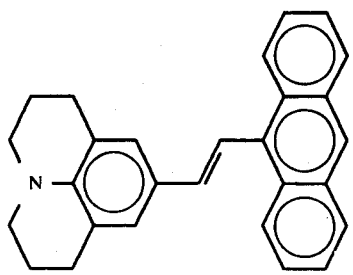
m.
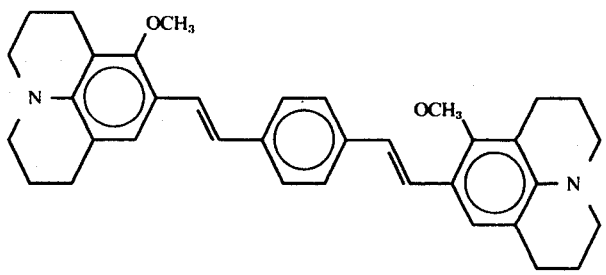
n.
* * * * *